(12) United States Patent
Kobilka et al.

(10) Patent No.: US 9,701,692 B1
(45) Date of Patent: Jul. 11, 2017

(54) SYNTHESIS OF THIENOTHIOPHENES

(71) Applicant: International Business Machines Corporation, Armonk, NY (US)

(72) Inventors: Brandon M. Kobilka, Tuscon, AZ (US); Joseph Kuczynski, North Port, FL (US); Jason T. Wertz, Pleasant Valley, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/068,440

(22) Filed: Mar. 11, 2016

(51) Int. Cl.
*C07D 495/04* (2006.01)

(52) U.S. Cl.
CPC .................................. *C07D 495/04* (2013.01)

(58) Field of Classification Search
CPC ..................................................... C07D 495/04
USPC .......................................................... 549/50
See application file for complete search history.

(56) References Cited

U.S. PATENT DOCUMENTS

| | | |
|---|---|---|
| 6,676,857 B2 | 1/2004 | Heeney et al. |
| 7,223,484 B2 | 5/2007 | Stossel et al. |
| 7,572,879 B2 | 8/2009 | Zahn et al. |
| 8,168,671 B2 | 5/2012 | Sotzing |
| 8,846,855 B2 | 9/2014 | He et al. |
| 8,906,520 B2 | 12/2014 | Seshadri |
| 8,927,684 B2 | 1/2015 | Li et al. |
| 9,006,568 B2 | 4/2015 | Wang et al. |
| 9,048,433 B2 | 6/2015 | Blouin et al. |
| 2004/0074779 A1 | 4/2004 | Sotzing |
| 2004/0229925 A1 | 11/2004 | Zhang |
| 2014/0151657 A1 | 6/2014 | Wang et al. |

FOREIGN PATENT DOCUMENTS

| | | |
|---|---|---|
| CN | 102286141 A | 12/2011 |
| CN | 104098758 A | 10/2014 |
| WO | 2014088795 A1 | 6/2014 |

OTHER PUBLICATIONS

Patrick S. Fier, et al., Copper-Mediated Fluorination of Aryl Iodides, Journal of the American Chemical Society, 2012, 134, pp. 10795-10798.
Yongye Liang, et al., Development of New Semiconducting Polymers for High Performance Solar Cells, American Chemical Society, 2009, 131, pp. 56-57.
Ji-Cheng Li, et al., Synthesis of a Benzothiadizole/thiophene-based Oligomer for Bulk Heterojunction Photovoltaic Cells, Synthetic Metals, 159, 2009, pp. 201-208.
Martijn M. Wienk, et al., Low Band Gap Polymer Bulk Heterojunction Solar Cells, 2006, 422, pp. 488-491.
Dawei Yue, et al., Synthesis of 2,3 Disubstituted Benzo[b]thiophenes via Palladium-Catalyzed Coupling and Electrophilic Cyclization of Terminal Acetylenes, Journal of Organic Chemistry, 2002, 67, pp. 1905-1909.
D. W. H. MacDowell, et al., Synthesis of 4,6-Dihydrothieno[3,4-b]thiophene, Journal of Organic Chemistry, 1996, 31 (11), pp. 3592-3595.
Francesco Babudri, et al., Fluorinated Organic Materials for Electronic and Optoelectronic Applications: the Role of the Fluorine Atom, Chemical Communications, 2007, 10, pp. 1003-1022.
Jianhui Hou, et al., Synthesis, Characterization, and Photovoltaic Properties of a Low Band Gap Polymer Based on Silole-Containing Polythiophenes and 2,1,3-Benzothiadiazole, Journal of the American Chemical Society, 2008, 130, pp. 16144-16145.
Yongye Liang, et al., Highly Efficient Solar Cell Polymers Developed via Fine-Tuning of Structural and Electronic Properties, Journal of the American Chemical Society, 2009, 131, pp. 7792-7799.
Zhicai He, et al., Enhanced Power-conversion Efficiency in Polymer Solar Cells Using an Inverted Device Structure, Nature Photonics, 2012, 6, pp. 591-595.
Tanmoy Dey, et al., Versatile Synthesis of 3,4-b Diheteropentalenes, Tetrahedron Letters, 2010, 51, pp. 2089-2091.
John D. Nguyen, et al., Engaging Unactivated Alkyl, Alkenyl and Aryl Iodides in Visible-light-mediated Free Radical Reactions, Nature Chemistry, 2012, 4, pp. 854-859.
Woo Jin Bae, et al., Synthesis and Photophysical Properties of Soluble Low-Bandgap Thienothiophene Polymers with Various Alkyl Side-Chain Lengths, Journal of Polymer Science Part A: Polymer Chemistry, 2011, 49, pp. 3260-3271.
David W. Hawkins, et al., Synthesis of thieno-[2,3-b]-, -[3,2-b]- and -'3,4-b]-thiophenes and thieno-[3',2':4,5]-, -[2',3':4,5]- and -[3',4':4,5]-thieno[3,2-d]pyrimidin-7(6H)-ones starting from thiophene, J. Chem. Soc., Perkin Trans. 1, 1994, pp. 2735-2743.
Yahia Nasser Mabkhot, et al., Synthesis of Thieno[2,3-b]thiophene Containing Bis-Heterocycles-Novel Pharmacophores, Int J Mol Sci. 2013, 14(3), pp. 5712-5722.

*Primary Examiner* — Taofiq A Solola
(74) *Attorney, Agent, or Firm* — Patterson + Sheridan, LLP

(57) ABSTRACT

In some embodiments, a method for synthesizing a compound of the structure:

is provided wherein R is selected from the group consisting of alkyl, ester, aryl, vinyl, ketone, amide, and sulfone, includes mixing a 3-(methylthio)-4-alkynylthiophene with iodine and/or iodine monochloride. In some embodiments, a method for synthesizing a compound of the structure:

is provided wherein R is selected from the group consisting of alkyl, ester, aryl, vinyl, ketone, amide, and sulfone, includes mixing a 3-bromo-4-(methylthio)-thiophene, a terminal alkyne, and a palladium catalyst.

18 Claims, 3 Drawing Sheets

SYNTHESIS OF THIENOTHIOPHENES

The present disclosure relates to organic photovoltaic monomers, oligomers, and polymers.

BACKGROUND

Organic electronics have drawn research interest in recent years because of their potential for broad commercial application, including electroluminescence devices, field effect transistors and organic photovoltaics (OPVs), etc. In all these devices, the key component is organic semiconducting material, which is usually used as one or more active thin layers. OPVs offer a practical path to achieve low-cost, renewable energy. OPVs have several advantages that their inorganic counterparts lack that allows for strong potential of lower cost implementation. The advantages of organic electronics include their ability to be solution processed into large-area thin-films, to be fabricated into lightweight and flexible devices, and the capacity to tune their properties through organic synthesis. To ultimately replace their inorganic, silicon-based counterparts, organic materials that give the highest possible power conversion efficiency (PCE) for the lowest possible cost are needed.

Among organic semiconductors, alternating conjugated polymers of an electron-donor (ED) unit and an electron-acceptor (EA) unit have attracted attention due to their special properties associated with the donor/acceptor (D/A) structure in the main chain. This D/A structure can effectively lower the band gap of conjugated polymers, especially for solar cell applications, where the polymer absorption can be fine-tuned to match the solar spectrum. Meanwhile, the energy offset between lowest unoccupied molecular orbital (LUMO) of the polymer and, for example, fullerene derivatives (widely used electron acceptors in organic solar cells) should be well controlled to be just enough to allow for charge separation in order to minimize energy loss. However, to fine tune the energy levels (highest occupied molecular orbital (HOMO), LUMO) of the conjugated polymer, while simultaneously optimizing other properties, such as solid state packing, solubility, carrier mobility still tends to be difficult.

One of the best performing classes of conjugated polymers is based on an ester functionalized thieno[3,4-b]thiophene (MTT) and alkoxy-substituted benzodithiophene (PTB1). Among these, the polymer with the highest, most regularly reported PCE is a fluorinated derivative of PTB1 (known as PTB7), synthesized from an F-MTT monomer, used in OPVs with over 9% efficiency.

MTT

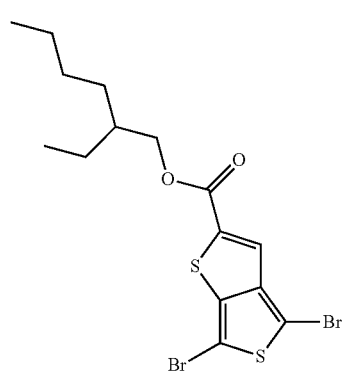

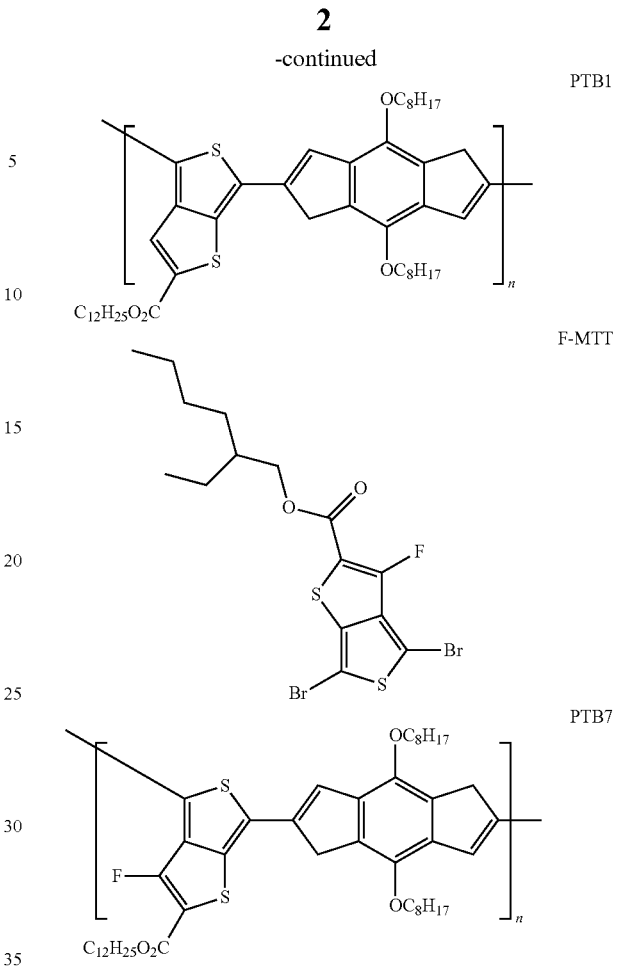

Fluorinated conjugated polymers show several advantages compared with their non-fluorinated counterparts. First, they usually have lower HOMO and LUMO energy levels, which will increase open circuit voltage of photovoltaic devices and endow the polymer better resistance against oxidative degradation processes. Second, because of high electronegativity of fluorine, the resulting polymers can be used as n-type or ambipolar semiconducting materials. Third, the fluorinated compounds can form C—H . . . F interactions in some instances, which can influence the solid state supramolecular organization, phase segregation and π-π stacking of the polymeric material. These features may enhance the charge carrier mobility. Despite these beneficial properties, the number of fluorinated monomers with strong electron withdrawing ability for use in OPVs is quite limited.

Additionally, synthesis of F-MTT, for example, involves many steps (11 steps), includes difficult chemistry, and significant amounts of purification, all of which contribute to PTB7 being one of the most expensive materials for OPVs. PTB7 sees widespread academic use, but is currently impractical for industrial scale production. When compared among other polymers and small molecules commonly used in OPVs, PTB1 is one of the most expensive in number of dollars per grams and per steps. PTB7 is slightly more expensive as it requires even more reagents and steps than PTB1. There is a need in the art for improved syntheses of organic photovoltaic monomers, oligomers, and polymers as well as a wider variety of OPV monomers.

SUMMARY

In some embodiments, a method for synthesizing a compound of the structure:

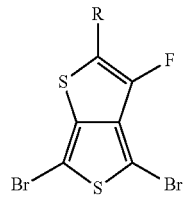

includes mixing a 3-(methylthio)-4-alkynylthiophene with iodine and/or iodine monochloride. R is selected from the group consisting of alkyl, ester, aryl, vinyl, ketone, amide, and sulfone.

In some embodiments, a method for synthesizing a compound of the structure:

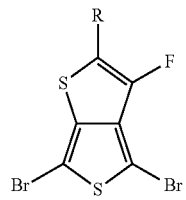

includes mixing a 3-bromo-4-(methylthio)-thiophene, a terminal alkyne, and a palladium catalyst. R is selected from the group consisting of alkyl, ester, aryl, vinyl, ketone, amide, and sulfone.

In some embodiments, a compound is of the structure:

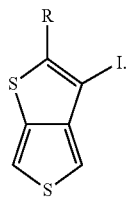

R is selected from the group consisting of alkyl, ester, aryl, vinyl, ketone, amide, and sulfone.

BRIEF DESCRIPTION OF THE DRAWINGS

So that the manner in which the above recited features of the present disclosure can be understood in detail, a more particular description of the present disclosure, briefly summarized above, may be had by reference to embodiments, some of which are illustrated in the appended drawings. It is to be noted, however, that the appended drawings illustrate only typical embodiments of present disclosure and are therefore not to be considered limiting of its scope, for the present disclosure may admit to other equally effective embodiments.

DETAILED DESCRIPTION

Figure 1:
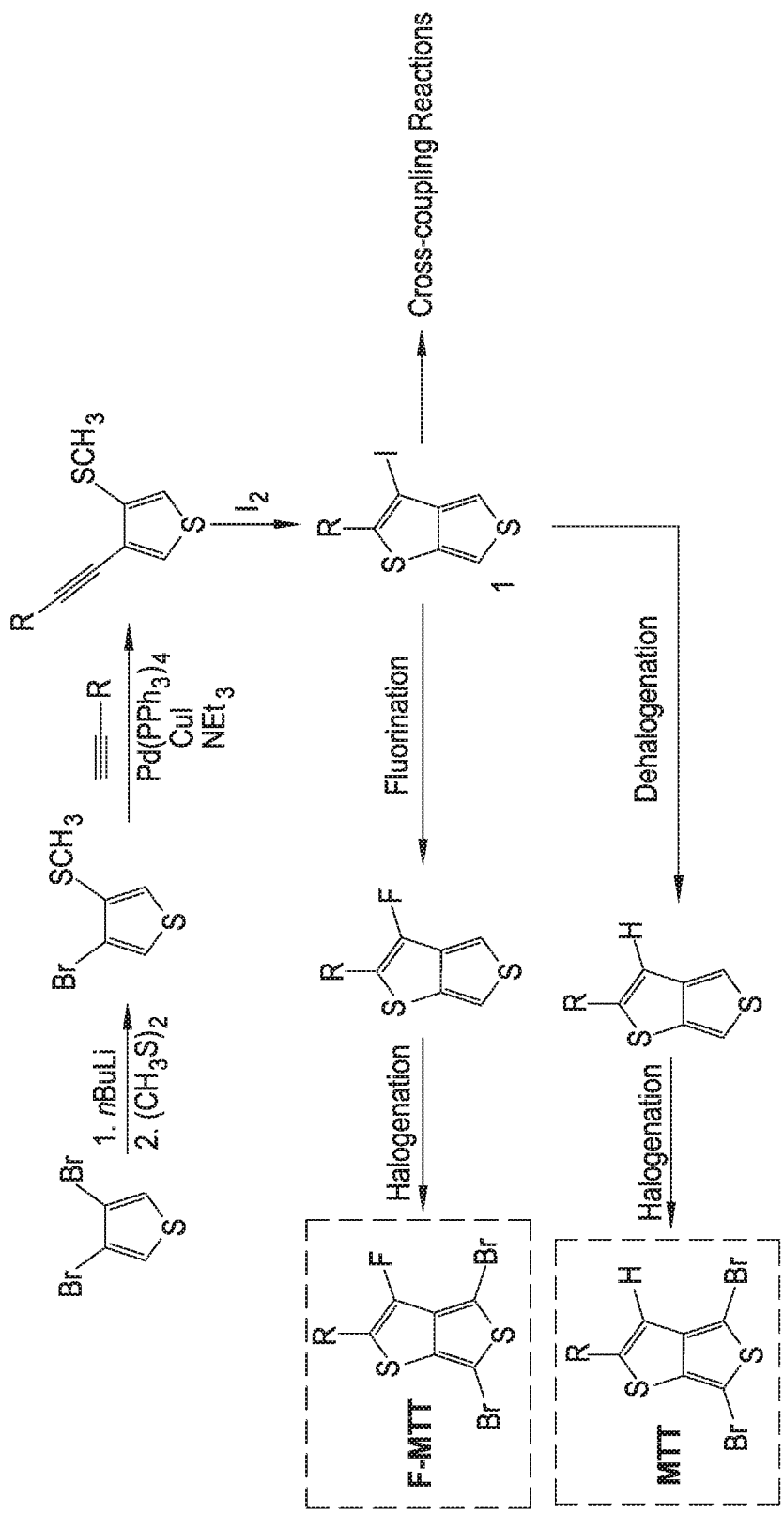
FIG. 1 is a scheme illustrating synthesis of MTT and F-MTT, according to some embodiments.

Syntheses of MTT and F-MTT described herein provide fewer reactions and purification steps than typical MTT and F-MTT syntheses. F-MTT and MTT syntheses described herein provide F-MTT and MTT products with higher overall yields (due to the fewer number of reactions and purifications as compared to typical syntheses). F-MTT and MTT syntheses described herein provide F-MTT and MTT products at much lower overall cost, as compared to typical F-MTT and MTT syntheses, due to the fewer number of reactions and purifications which allows fewer purchases/syntheses of starting materials, reaction solvents, extraction media, recrystallization solvents, solid phase material for chromatography, energy input to a distillation apparatus, etc. The cost advantage and reduced overall amounts of material render syntheses of MTT and F-MTT (and derivatives thereof) amenable for industrial application/scale-up. Furthermore, reagents such as $SnCl_2$ (and byproducts thereof) and oxalyl chloride can be avoided using MTT and F-MTT syntheses described herein. Furthermore, 3-iodo-thieno-[3,4-b]-thiophene (1) is a versatile compound/intermediate that can be transformed into MTT, F-MTT, and derivatives thereof useful for small molecule and polymer photovoltaic applications.

As described herein, the terms "substituent", "radical", "group", "moiety" and "fragment" may be used interchangeably to indicate a point of attachment to a molecule.

As described herein, "alkyl" embraces a linear or branched acyclic alkyl radical containing from 1 to about 16 carbon atoms. In some embodiments, alkyl is a $C_{1-10}$ alkyl, $C_{1-7}$ alkyl or $C_{1-5}$ alkyl radical. Examples of alkyl include methyl, ethyl, propyl, isopropyl, butyl, isobutyl, tert-butyl, sec-butyl, pentan-3-yl.

As described herein, "ester" embraces the structure:

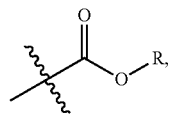

where R may be, for example, alkyl or aryl.

As described herein, "sulfonyl" embraces a radical having the structure:

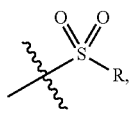

where R may be, for example, H, alkyl, or aryl.

As described herein, "amide" embraces the structure:

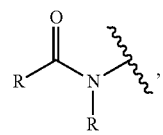

where each instance of R may independently be, for example, H, alkyl, or aryl.

As described herein, "vinyl" embraces an unsaturated, acyclic hydrocarbon radical with at least one double bond. In some embodiments, vinyl contains from 2 to about 16 carbon atoms. Examples of vinyl include alkenyl such as propenyl, butenyl and pentenyl. When cis/trans (or Z/E) configuration is not expressly defined for a chemical compound, radical, ion, or other species, and the species may have cis and trans isomers, both cis/trans isomers are embraced. For example, the term "propenyl" embraces both (E)-propenyl and (Z)-propenyl and the term "butenyl" embraces both (E)-butenyl and (Z)-butenyl.

As described herein, "terminal alkyne" embraces an alkyne containing the moiety:

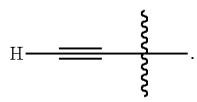

As described herein, "halo" refers to fluoro (—F), chloro (—Cl), bromo (—Br), or iodo (—I).

As described herein, "triflate" refers to trifluoromethanesulfonate and is abbreviated as "Tf".

As described herein, the structure:

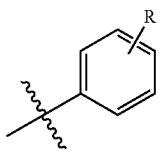

embraces one or more of ortho-, meta-, and para-substituted isomers. The structure also embraces one or more of mono-, di-, tri-, tetra-, and penta-R-substituted isomers. R may be any suitable substituent.

In some embodiments, a method for synthesizing F-MTT or F-MTT derivative of the structure:

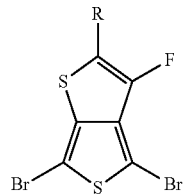

includes mixing a 3-(methylthio)-4-alkynylthiophene with iodine and/or iodine monochloride. R may be alkyl, ester, aryl, vinyl, ketone, amide, or sulfone. The mixing forms a 3-iodo-thieno-[3,4-b]thiophene of the structure:

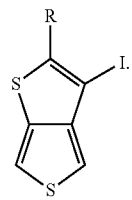

R may be alkyl, ester, aryl, vinyl, ketone, amide, or sulfone. In some embodiments, a 3-(methylthio)-4-alkynylthiophene is formed by mixing a 3-bromo-4-(methylthio)-thiophene, a terminal alkyne, and a palladium catalyst. The palladium catalyst may be Pd(PPh$_3$)$_4$. Copper iodide and an amine (such as a base, such as triethylamine or tributylamine) may be mixed with the 3-bromo-4-(methylthio)-thiophene, the terminal alkyne, and the palladium catalyst.

The 3-bromo-4-(methylthio)-thiophene may be formed by mixing 3,4-dibromo-thiophene with n-butyl lithium to form a first mixture followed by adding dimethyl disulfide to the first mixture to form a second mixture.

In some embodiments, a 3-(methylthio)-4-alkynylthiophene is selected from the group consisting of:

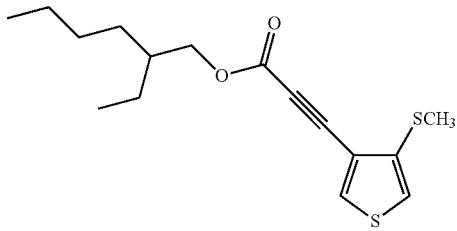

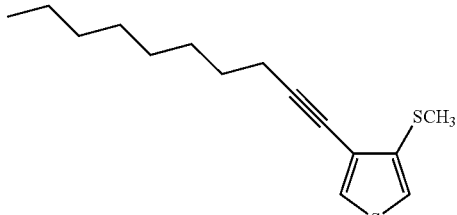

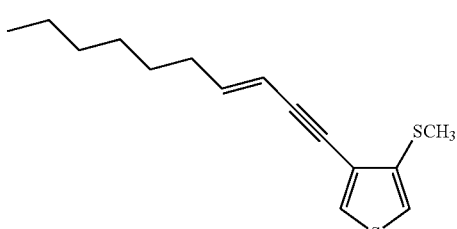

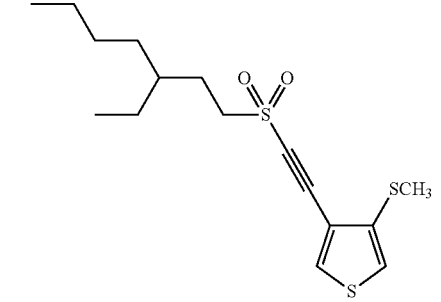

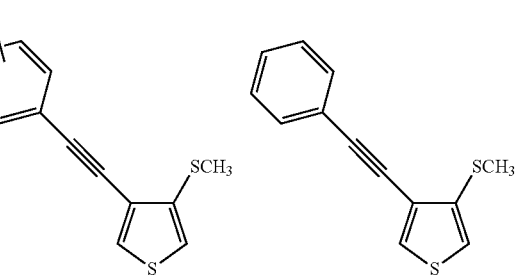

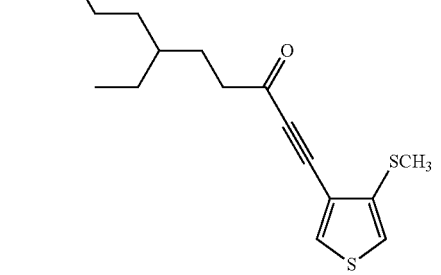

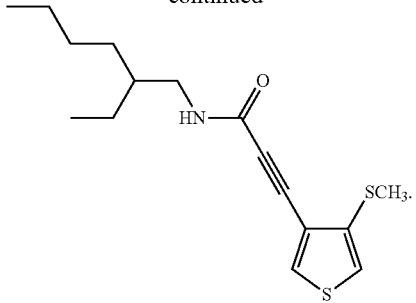

In some embodiments, a 3-iodo-thieno-[3,4-b]thiophene is selected from the group consisting of:

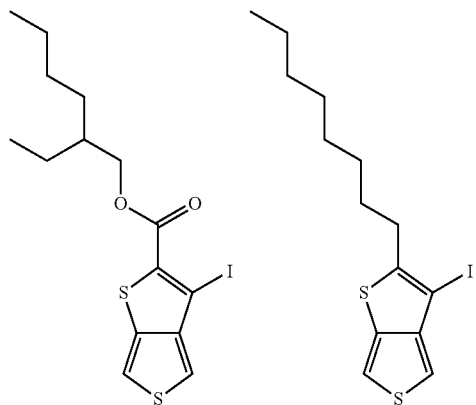

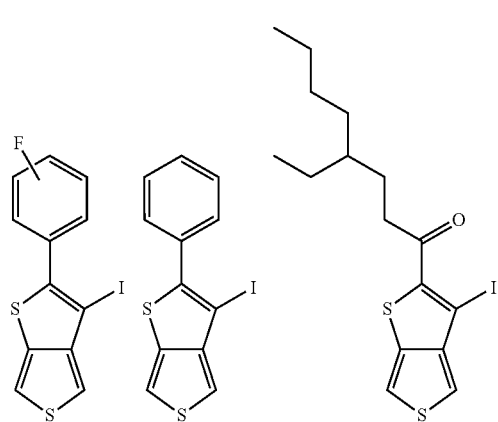

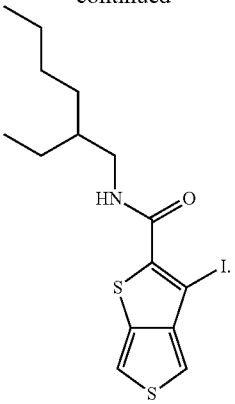

In some embodiments, a method includes fluorinating a 3-iodo-thieno-[3,4-b]thiophene to form a 3-fluoro-thieno-[3,4-b]thiophene. The fluorinating may include mixing the 3-iodo-thieno-[3,4-b]thiophene with silver fluoride and a copper catalyst. The copper catalyst may be (t-BultylCN)$_2$CuOTf (Tf=triflate or trifluoromethanesulfonate —F$_3$CSO$_3$). In some embodiments, the fluorinating includes mixing 3-iodo-thieno-[3,4-b]-thiophene with 3 molar equivalents of (t-ButylCN)$_2$CuOTf and 2 molar equivalents of silver fluoride in N,N-dimethylformamide solvent to form a mixture, and heating the mixture to between about 110° C. and about 170° C. Cesium fluoride may be mixed with the 3-iodo-thieno-[3,4-b]thiophene, the silver fluoride, and the copper catalyst.

A method may include mixing a 3-fluoro-thieno-[3,4-b]thiophene with a halogenating agent to form F-MTT or an F-MTT derivative. The halogenating agent may be N-bromosuccinimide or bromine.

In some embodiments, a method for synthesizing F-MTT or MTT derivative of the structure:

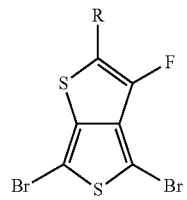

includes mixing a 3-bromo-4-(methylthio)-thiophene, a terminal alkyne, and a palladium catalyst. R may be alkyl, ester, aryl, vinyl, ketone, amide, and sulfone. The method may include mixing a 3-(methylthio)-4-alkynylthiophene with iodine and/or iodine monochloride.

In some embodiments, a 3-iodo-thieno-[3,4-b]thiophene has the structure

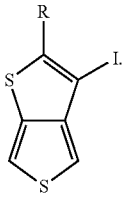

R may be selected from the group consisting of alkyl, ester, aryl, vinyl, ketone, amide, and sulfone. In some embodiments, R is substituted with one or more electron withdrawing group(s). The electron withdrawing group(s) may be halo, —CF$_3$, or nitro. In some embodiments, R is substituted with an electron donating group. The electron donating group may be alkyl, such as C1-C6 alkyl, or alkoxy, such as C1-C6 alkoxy.

In some embodiments, the 3-iodo-thieno-[3,4-b]thiophene is selected from the group consisting of:

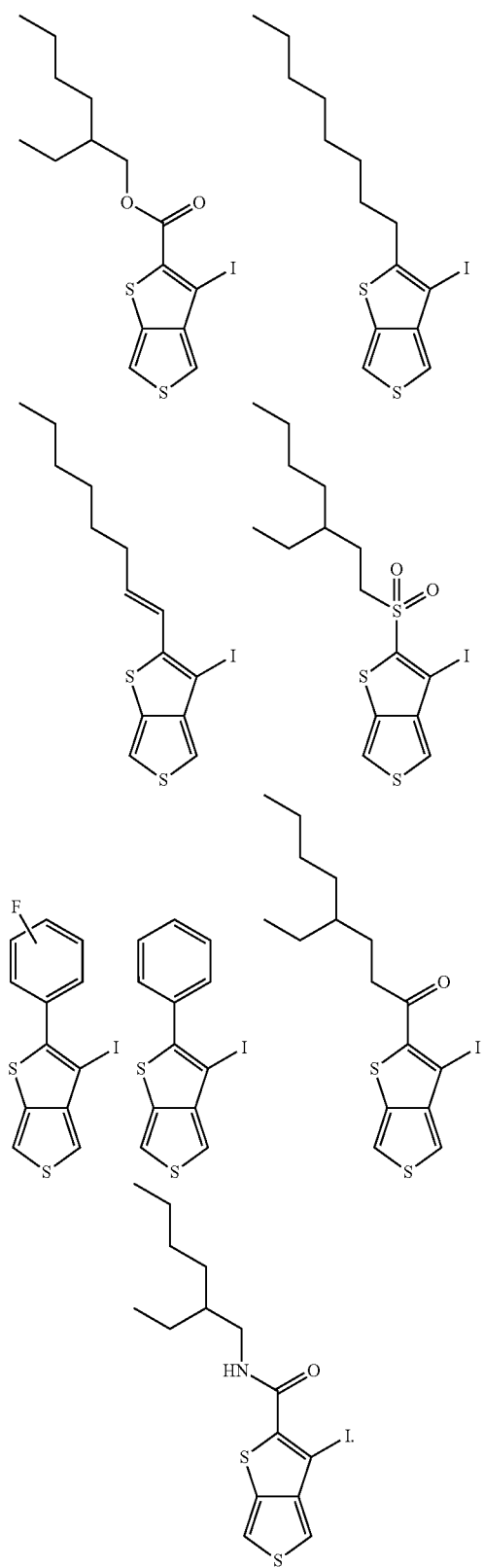

FIG. 1 is a scheme illustrating synthesis of MTT and F-MTT, according to some embodiments. As shown in FIG. 1, a one pot lithium-halogen exchange and subsequent methylthiolation is carried out with 3,4-dibromo-thiophene treated with n-butyl lithium (n-BuLi) followed by addition of dimethyl disulfide ((MeS)$_2$, where "Me" is methyl) to yield 3-bromo-4-(methylthio)-thiophene. 3-bromo-4-(methylthio)-thiophene may be purified by extraction and distillation. Starting materials, such as 3,4-dibromo-thiophene, may be obtained by Oakwood Products, Inc. or Sigma-Aldrich, Co. In some embodiments, (MeSe)$_2$, dimethyl diselenide, may be used instead of or in addition to (MeS)$_2$ to yield 3-bromo-4-(methylselenium)-thiophene, with the remainder of the scheme of FIG. 1 carried out accordingly.

3-bromo-4-(methylthio)-thiophene may undergo a Sonogashira cross-coupling reaction (for example by reacting a terminal alkyne in the presence of Pd(PPh$_3$)$_4$, copper iodide (CuI), and triethylamine (NEt$_3$) where Et="ethyl") to yield 3-(methylthio)-4-alkynylthiophene. 3-(methylthio)-4-alkynylthiophene may be purified by distillation. 'R' includes alkyl, ester, aryl, vinyl, ketone, amide, and sulfonyl, where 'R' is unsubstituted or substituted with an electron withdrawing group or electron donating group. Electron donating groups include alkyl and alkoxy. Electron withdrawing groups include halo, —CF$_3$, and nitro.

In some embodiments, 3-(methylthio)-4-alkynylthiophene includes:

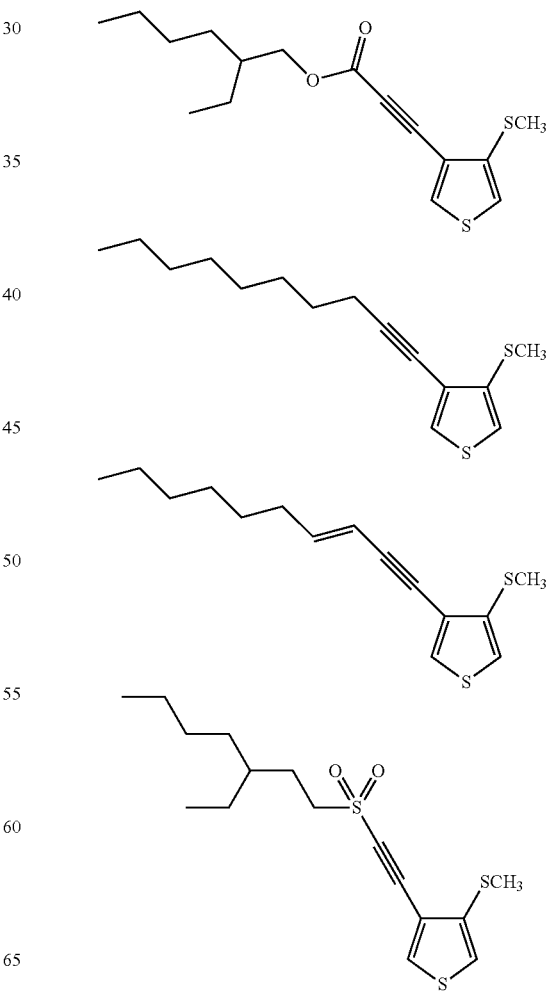

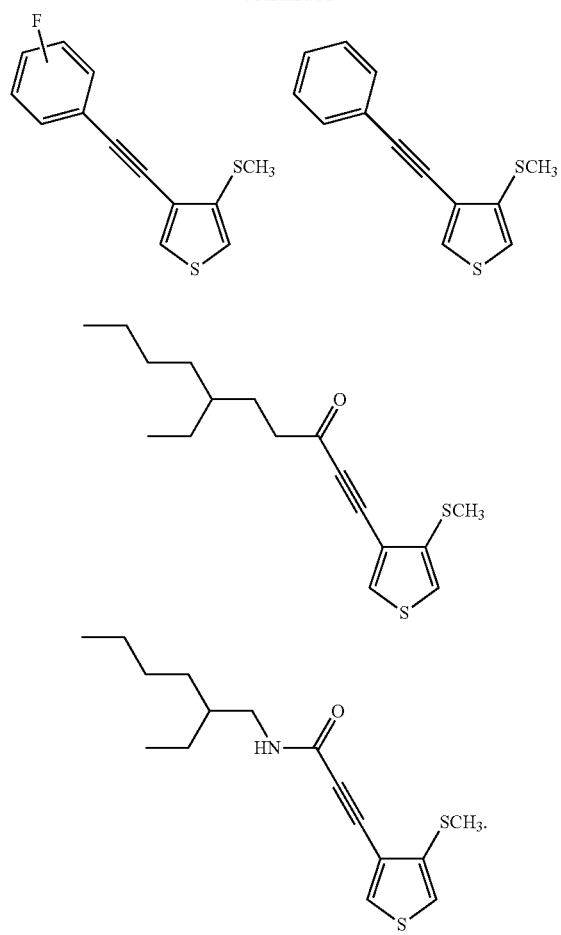
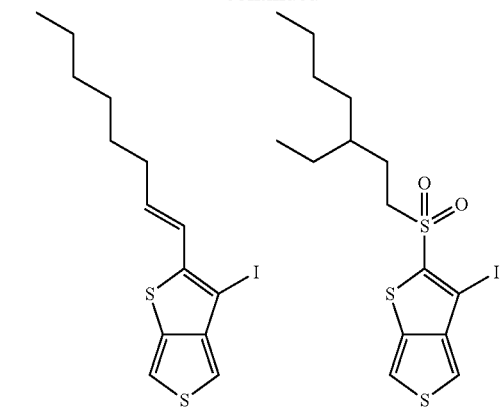
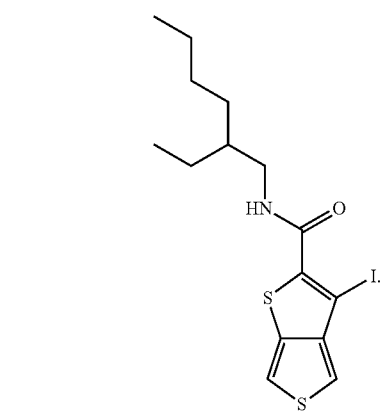

As shown in FIG. 1, 3-(methylthio)-4-alkynylthiophene may be cyclized upon treatment with iodine (I$_2$) to yield 3-iodo-thieno-[3,4-b]-thiophene (1). Alternatively, 3-(methylthio)-4-alkynylthiophene may be cyclized upon treatment with iodine monochloride (ICl) to yield 3-iodo-thieno-[3,4-b]-thiophene (1). 3-iodo-thieno-[3,4-b]thiophene (1) may be purified by recrystallization. This reaction provides an aromatic heterocycle (thieno-[3,4-b]-thiophene) and creates an aryl-iodide "synthetic handle" in one reaction.

Examples of 3-iodo-thieno-[3,4-b]thiophene (1) include:

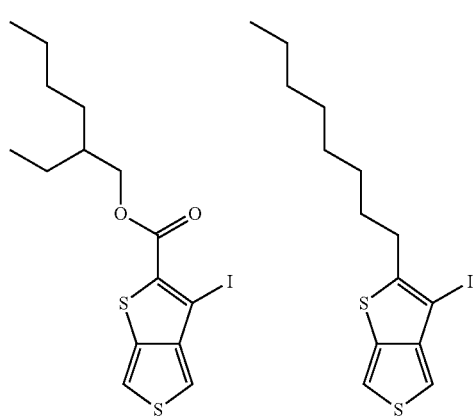

The 3-iodo-thieno-[3,4-b]-thiophene (1) is a versatile compound/intermediate. As shown in FIG. 1, 3-iodo-thieno-[3,4-b]thiophene (1) may undergo a fluorination reaction to yield 3-fluoro-thieno-[3,4-b]thiophene. The 3-fluoro-thieno-[3,4-b]thiophene may be halogenated to yield F-MTT. A suitable fluorination reaction includes treating 3-iodo-thieno-[3,4-b]thiophene (1) with silver (I) fluoride (AgF) in the presence of a copper catalyst ([Cu]) in a solvent such as DMF or dimethylsulfoxide (DMSO) to yield 3-fluoro-thieno-[3,4-b]thiophene.

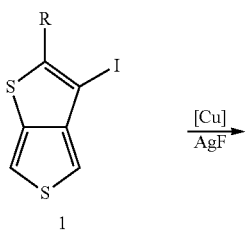

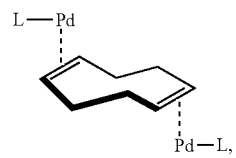

where L is of the structure:

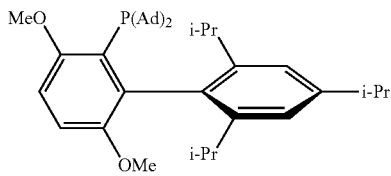

or

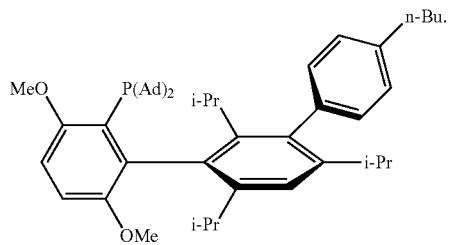

As used herein, "Ad" denotes "adamantyl", "Me" denotes "methyl", "i-Pr" denotes "isopropyl", and "n-Bu" denotes "n-butyl".

The 3-fluoro-thieno-[3,4-b]thiophene may be purified by extraction and/or recrystallization. In some embodiments, fluorination reaction conditions include treating 3-iodo-thieno-[3,4-b]-thiophene (1) with 3 equivalents of (t-Bu CN)$_2$CuOTf and 2 equivalents of AgF in DMF solvent at 140° C. for about 22 hours. In some embodiments, cesium fluoride (CsF) is included in the fluorination reaction in addition to or as a substitute of AgF.

A suitable halogenation reaction includes treating 3-fluoro-thieno-[3,4-b]thiophene with a brominating agent (such as N-bromosuccinimide and/or bromine (Br$_2$)) in a solvent, such as DMF) to yield F-MTT. F-MTT may be purified by column chromatography. For organic synthesis generally, purification steps include acid/base/water neutralization, extraction (organic/aqueous), column chromatography, recrystallization, and distillation. These purification methods vary in cost, typically with chromatography being the most expensive. More purification needed in an overall reaction scheme, and for a particular compound in the scheme, results in higher cost of the overall synthesis and slower throughput of synthesis of the final product. Synthesis of F-MTT shown in FIG. 1 involves 5 reactions and 6 or 7 purification steps, significantly fewer than the number of reactions and purification steps of typical F-MTT synthesis (33% of the purification for F-MTT synthesis shown in FIG. 3 (described below) and half of the purification for MTT synthesis shown in FIG. 2 (described below)). Additionally, synthesis of F-MTT as shown in FIG. 1 includes only one column chromatography purification (which, in some embodiments, may be replaced by other purification techniques). Furthermore, reagents such as SnCl$_2$ (and byproducts thereof) and oxalyl chloride can be avoided using the syntheses of F-MTT and MTT described in FIG. 1.

Other suitable fluorination reactions include treating 3-iodo-thieno-[3,4-b]thiophene (1) with phenyl lithium in diethyl ether, THF, and/or cyclohexane at below 0° C., such as −28° C., followed by addition of N-fluorobenzenesulfonimide (NFSI) in THF. Phenyl lithium may be formed in situ from a halobenzene and n-BuLi.

In some embodiments, fluorination is performed by treating 3-iodo-thieno-[3,4-b]thiophene (1) with AgF (such as 2 eq.) and KF (such as 0.5 eq.) in cyclohexane with between about 1 mol % and about 5 mol %, such as 2 mol %, of a catalyst. The reaction may be performed at between about 23° C. and about 130° C. If temperature is increased from room temperature, such as at about 130° C., the reaction may be held at the increased temperature for between about 3 hours and about 20 hours, such as about 14 hours. In some embodiments, the catalyst includes a palladium catalyst, such as of the structure:

In some embodiments, fluorination is performed by treating 3-iodo-thieno-[3,4-b]thiophene (1) with AgF (such as 1.5 eq.) in toluene in the presence of (COD)Pd(CH$_2$TMS)$_2$ and 2-(Dicyclohexylphosphino)3,6-dimethoxy-2',4',6'-triisopropyl-1,1'-biphenyl (hereinafter, "BrettPhos"). As used herein, "COD" denotes "cyclooctadiene" and "TMS" denotes "trimethylsilyl". The temperature of this reaction mixture may be increased to promote the fluorination reaction. After complete or substantial formation of 3-fluoro-thieno-[3,4-b]thiophene, the reaction mixture may be filtered through a glass filter and/or a plug of Celite® to remove all solids.

In some embodiments, 3-iodo-thieno-[3,4-b]thiophene (1) is halogenated (with bromine) before fluorination of the iodo moiety. Such a reaction scheme is as follows:

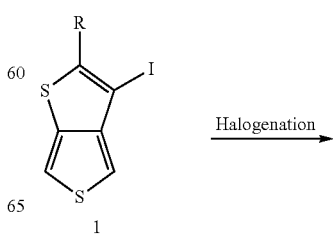

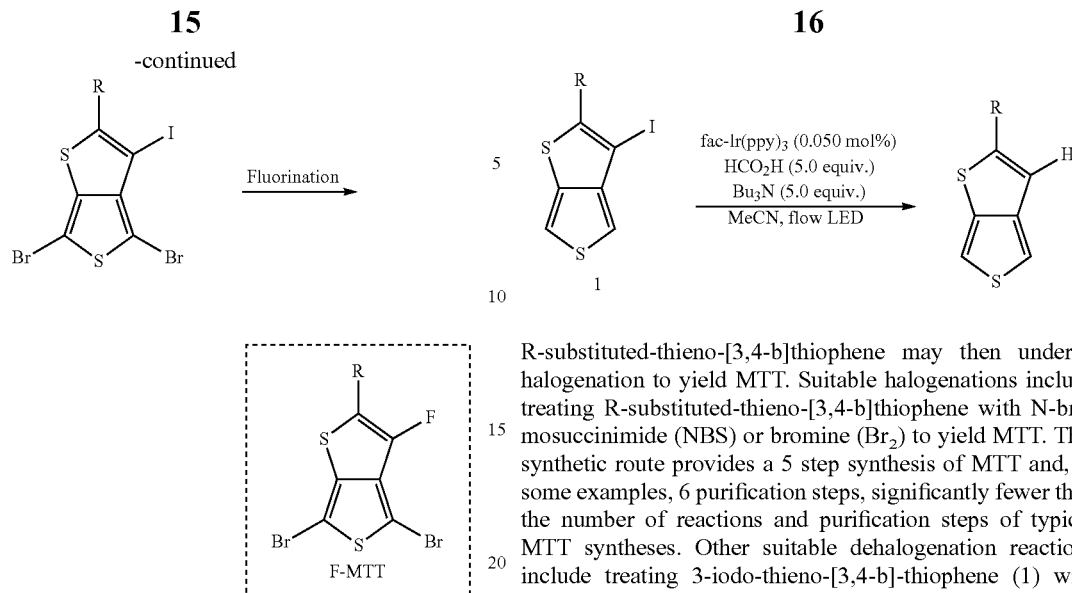

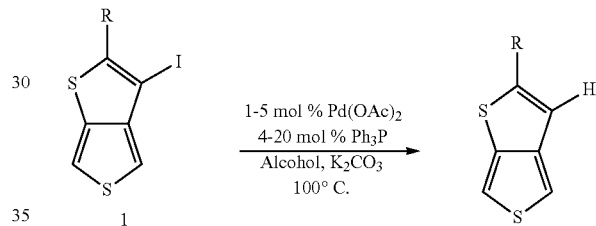

Suitable halogenation reactions are as described above. Suitable fluorination reactions include treating 3-iodo-thieno-[3,4-b]dibromothiophene with Me$_4$NF in dimethyl sulfoxide. The temperature of this reaction mixture may be increased to promote the fluorination reaction.

Alternatively, 3-iodo-thieno-[3,4-b]dibromothiophene is treated with substoichiometric amounts (for example about 3 mol %) of a catalyst such as [Rh(COD)(MeCN)$_2$]BF$_4$ in DMF, and addition of triethylamine (for example, 3 eq.) and triethoxysilane (for example, 2 eq.) to yield a reaction product. The temperature of the reaction mixture may be increased to, for example, about 80° C. for about 2 hours. The reaction mixture may be purified by extraction with water and an organic solvent such as diethyl ether. The organic solvent phase may be dried with Na$_2$SO$_4$ or MgSO$_4$, filtered, and concentrated under reduced pressure, giving purified reaction product. This reaction product may be dissolved in acetone, followed by addition of silver oxide (for example, about 2 eq.), barium oxide (for example, about 1.1 eq.), and 1-chloromethyl-4-fluoro-1,4-diazoniabicyclo [2.2.2]-octane bis(trifluoroborate) (for example, about 2 eq.). The temperature of the reaction mixture may be increased to, for example, about 90° C. for about 2 hours. The reaction mixture may be cooled to room temperature and concentrated under reduced pressure to form a residue. To the residue may be added dichloromethane to form a solution. The solution may be filtered through a pad of Celite® and the filtrate may be then purified by chromatography or recrystallization.

Alternatively, as shown in FIG. 1, 3-iodo-thieno-[3,4-b] thiophene (1) may be dehalogenated to form R-substituted-thieno-[3,4-b]thiophene. A suitable dehalogenation includes treating 3-iodo-thieno-[3,4-b]-thiophene (1) with an iridium catalyst, such as fac-Ir(ppy)$_3$, formic acid (HCO$_2$H), and tributylamine (Bu$_3$N) in a suitable solvent such as acetonitrile (MeCN). The reaction may be promoted using a flow light emitting diode or visible light. As used herein, fac-Ir(ppy)$_3$ denotes tris[2-phenylpyridinato-C2,N]iridium(III).

R-substituted-thieno-[3,4-b]thiophene may then undergo halogenation to yield MTT. Suitable halogenations include treating R-substituted-thieno-[3,4-b]thiophene with N-bromosuccinimide (NBS) or bromine (Br$_2$) to yield MTT. This synthetic route provides a 5 step synthesis of MTT and, in some examples, 6 purification steps, significantly fewer than the number of reactions and purification steps of typical MTT syntheses. Other suitable dehalogenation reactions include treating 3-iodo-thieno-[3,4-b]-thiophene (1) with Palladium (II) acetate (Pd(OAc)$_2$), triphenyl phosphine (Ph$_3$P), and potassium carbonate in a solvent, such as an alcohol. The reaction may be heated to promote the formation of R-substituted-thieno-[3,4-b]thiophene.

Alternatively, dehalogenation may be performed by treating 3-iodo-thieno-[3,4-b]-thiophene (1) with ammonium formate (for example, about 1 eq.) and a catalyst, such as trimetallic Pt/Pd/Fe nanoparticles in an organic solvent, such as methanol. Purification may be carried out by centrifugation of solid particles and washing of the remaining solution with acetone. Alternatively, dehalogenation may be performed by treating 3-iodo-thieno-[3,4-b]-thiophene (1) with Cs$_2$CO$_2$ and Pd(OAc)$_2$ in DMSO. The reaction mixture may be heated to, for example, about 80° C. for about 12 hours. Purification may be carried out by filtering the reaction mixture through a plug of Celite® and extracting the filtrate with dichloromethane and water, followed by concentrating the organic phase under reduced pressure.

F-MTT and MTT syntheses, such as those shown in FIG. 1, yield F-MTT and MTT products with higher overall yields (due to the fewer number of reactions and purifications as compared to the typical syntheses). F-MTT and MTT syntheses, such as those shown in FIG. 1, yield F-MTT and MTT products at much lower overall cost, as compared to typical F-MTT and MTT syntheses, due to the fewer number of reactions and purifications which allows fewer purchases/syntheses of starting materials, reaction solvents, extraction media, recrystallization solvents, solid phase material for chromatography, energy input to a distillation apparatus, etc.

3-iodo-thieno-[3,4-b]thiophene (1) may also undergo a wide range of cross-coupling reactions to obtain many versatile reaction products. Suitable cross-coupling reactions using 3-iodo-thieno-[3,4-b]thiophene (1) include Sonogashira, Suzuki, Negishi, Buchwald-Hartwig amination, Stille, Heck, Castro-Stephens, Kumada (via Grignard formation of (1)), Hiyama, Ullmann reaction, and Mac-Millan cross-couplings, among others. Cross-coupling reactions using 3-iodo-thieno-[3,4-b]thiophene (1) allows access to a large number of fluorinated compounds that can then undergo halogenation (as described above) to yield MTT/F-MTT derivatives. For example, 3-iodo-thieno-[3,4-b]thiophene (1) may undergo a Suzuki coupling reaction with mono- or poly-fluorinated phenyl boronic acids (—B(OH)$_2$, pinnacol protected, or 9-BBN protected). In some embodiments, 3-iodo-thieno-[3,4-b]thiophene (1) may undergo a Suzuki cross-coupling and subsequent halogenation, such as:

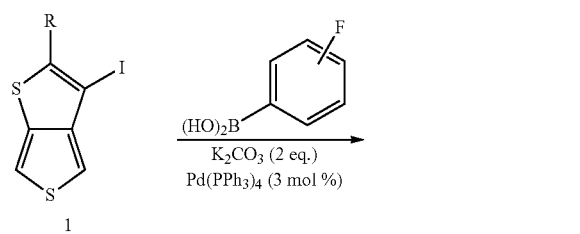

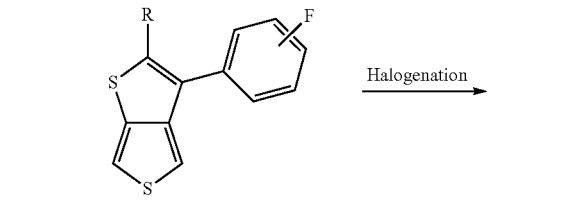

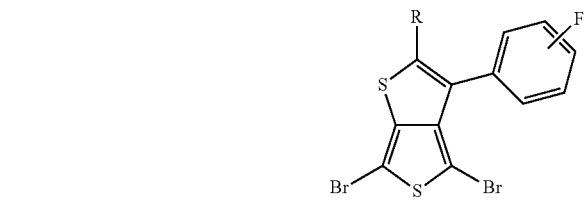

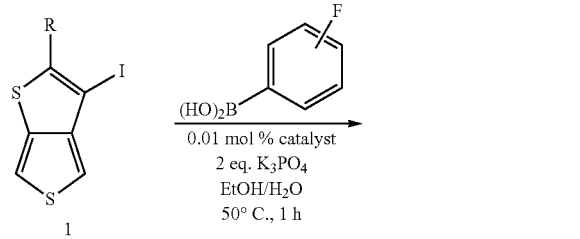

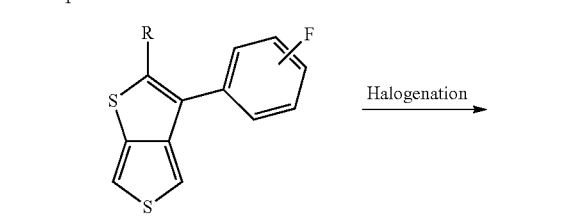

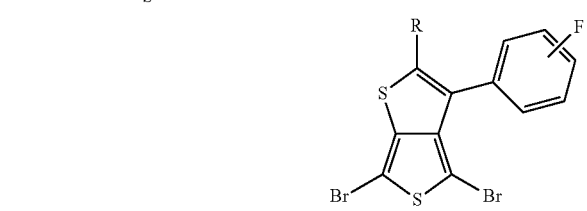

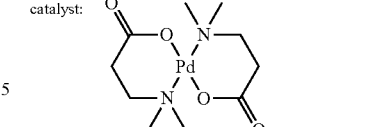

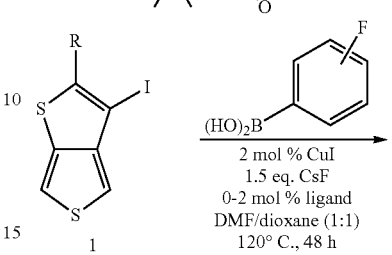

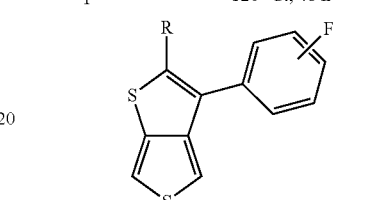

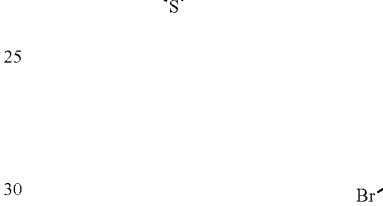

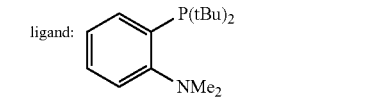

3-iodo-thieno-[3,4-b]thiophene (1) may be cross-coupled with poly-boronic acids, such as di-boronic acids and tri-boronic acids, to form MTT/F-MTT oligomers. The oligomers may be subsequently halogenated, for example, as described above. In some embodiments, 3-iodo-thieno-[3,4-b]thiophene (1) may undergo a Suzuki cross-coupling with a poly-boronic acid, such as:

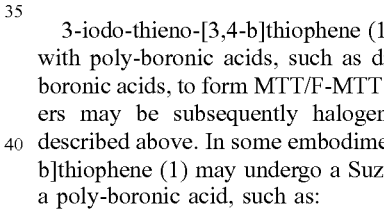

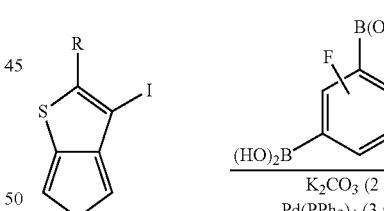

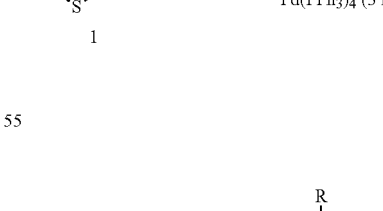

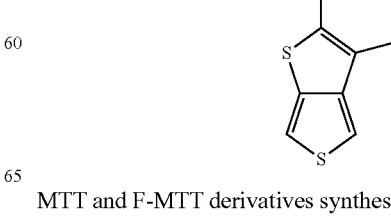

MTT and F-MTT derivatives synthesized via cross-coupling reactions of 3-iodo-thieno-[3,4-b]thiophene (1) allow access to a diverse array of MTT and F-MTT derivatives that may be used in small molecule photovoltaic devices.

Furthermore, acceptor molecules MTT and F-MTT (and derivatives) described herein may be reacted with donor molecules to form copolymers that may be used in organic photovoltaics. Suitable donor molecules include thiophenes (including diethiophene, terthiophene, and quaterthiophene), furans, selenophenes benzodifurans, benzodithiophenes, such as and 2,6-bis(trimethyltin)-4,8-dioctylbenze[1,2-b;4,5-b']dithiophene and 2,6-bis(trimethyltin)-4,8-dioctyoxylbenze[1,2-b;4,5-b']dithiophene, cyclopentathienodithiophenes, dithienosiloles, dithienopyrroles, carbazoles, diethienothiophenes, and silafluorenes.

The reactions shown in FIG. 1 may be carried out in the presence of a solvent, such as an organic solvent. A solvent may be used to adjust the rate of a reaction by decreasing or increasing the concentration(s) of the reactants. The organic solvent may be polar protic or polar aprotic. Polar aprotic solvents include dichloromethane (DCM), dimethylsulfoxide (DMSO), N,N-dimethylformamide (DMF), N,N-dimethylacetamide (DMA), and mixtures thereof. Polar protic solvents include ethanol and methanol.

Compounds described herein embrace the corresponding salts, tautomers, geometric isomers, stereoisomers, cis- and trans-geometric isomers (Z- and E-geometric isomers), R- and S-enantiomers, diastereomers, d-isomers, I-isomers, atropisomers, epimers, conformers, rotamers, mixtures of isomers and racemates thereof, as falling within the scope of the present disclosure.

Comparative Example of MTT Synthesis

Figure 2:
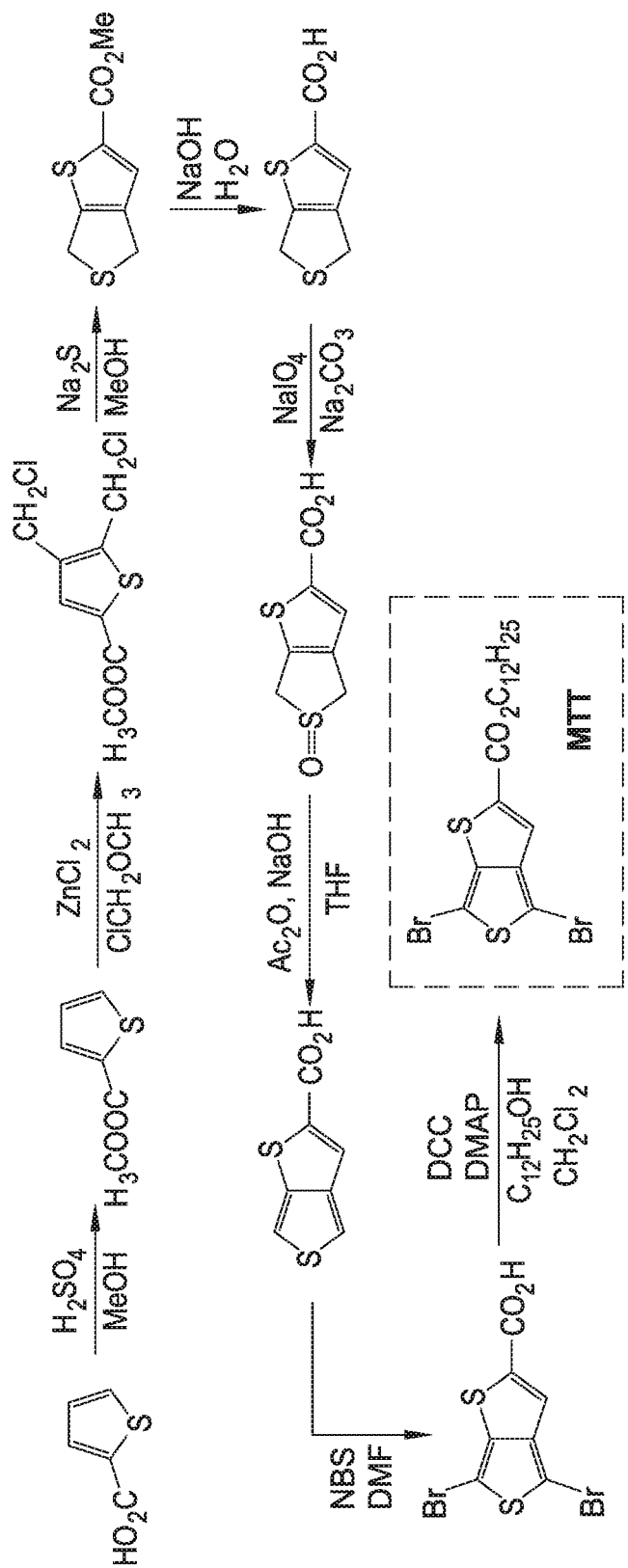
FIG. 2 is a scheme illustrating a typical comparative synthesis of MTT.

FIG. 2 is a scheme illustrating a typical synthesis of MTT. As shown in FIG. 2, 2-thiophene carboxylic acid is treated with sulfuric acid and methanol to yield 2-thiophene methyl ester. The 2-thiophene methyl ester is methylchlorinated by reaction with chloromethyl methyl ether (MOMCl) ($ClCH_2OCH_3$) in the presence of zinc (II) chloride ($ZnCl_2$) to yield di-(methylenechloro)-2-thiophene methyl ester. MOMCl is formed in situ by reacting formaldehyde dimethyl acetal with pentanoyl chloride. The di-(methylenechloro)-2-thiophene methyl ester is then treated with sodium sulfate ($Na_2S$) in methanol (MeOH)($CH_3OH$) to yield 4,6-dihydrothieno-[3,4-b]-thiophene methyl ester. The methyl ester is then hydrolyzed in the presence of sodium hydroxide (NaOH) to yield 4,6-dihydrothieno-[3,4-b]-thiophene carboxylic acid. The 4,6-dihydrothieno-[3,4-b]-thiophene carboxylic acid then forms a thiocarbonyl-containing compound upon treatment with sodium periodate ($NaIO_4$) and sodium carbonate ($Na_2CO_3$). The thiocarbonyl-containing compound undergoes cyclization upon treatment with acetic anhydride ($Ac_2O$) and sodium hydroxide (NaOH) in tetrahydrofuran (THF) solvent to yield thieno-[3,4-b]-thiophene carboxylic acid. The thieno-[3,4-b]-thiophene carboxylic acid is then treated with N-bromosuccinimide (NBS) in dimethylformamide (DMF) to yield thieno-[3,4-b]-(dibromothiophene) carboxylic acid. The carboxylic acid then undergoes esterification with n-dodecanol ($C_{12}H_{25}OH$) in the presence of N,N-dicyclohexylcarbodiimide (DCC) and 4-dimethylaminopyridine (DMAP) in dichloromethane (DCM) solvent to form MTT. Overall, the synthesis of MTT shown in FIG. 2 involves at least 9 reactions (including formation of MOMCl), and MTT synthesis shown in FIG. 2 involves 14 purification steps (4 neutralizations, 4 extractions, 1 column chromatograph, 4 recrystallizations and 1 distillation).

Comparative Example of F-MTT Synthesis

Figure 3:
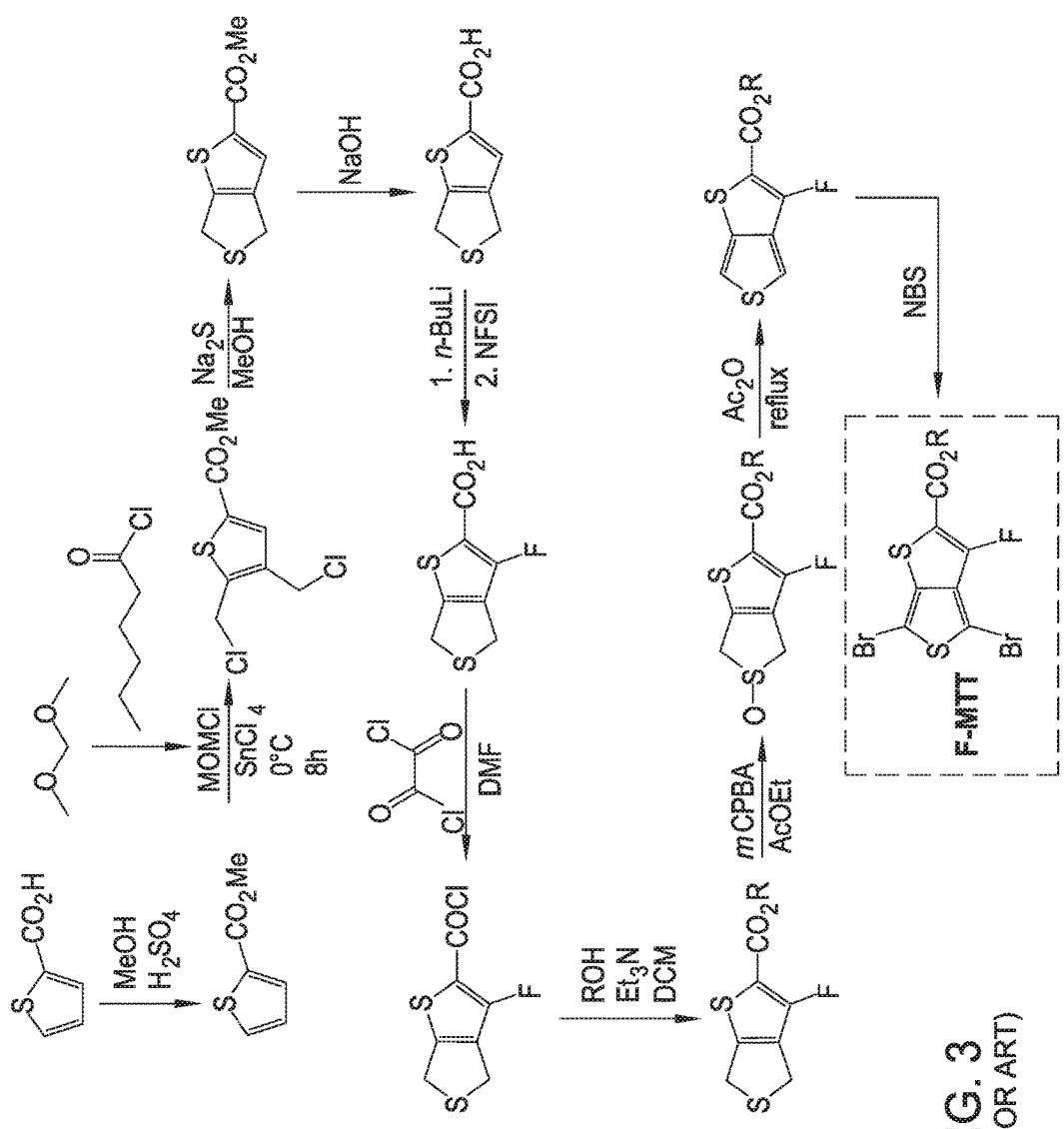
FIG. 3 is a scheme illustrating a typical comparative synthesis of F-MTT.

FIG. 3 is a scheme illustrating a typical synthesis of F-MTT. As shown in FIG. 3, 2-thiophene carboxylic acid is treated with sulfuric acid and methanol to yield 2-thiophene methyl ester. The 2-thiophene methyl ester is methylchlorinated by reaction with chloromethyl methyl ether (MOMCl) ($ClCH_2OCH_3$) in the presence of tin (IV) chloride ($SnCl_4$) at 0° C. for 8 hours to yield di-(methylchloro)-2-thiophene methyl ester. MOMCl is formed in situ by reacting formaldehyde dimethyl acetal with pentanoyl chloride. The di-(methylchloro)-2-thiophene methyl ester is then treated with sodium sulfate ($Na_2S$) in methanol (MeOH; $CH_3OH$) to yield 4,6-dihydrothieno-[3,4-b]-thiophene methyl ester. The methyl ester may then undergo hydrolysis in the presence of sodium hydroxide (NaOH) to yield 4,6-dihydrothieno-[3,4-b]-thiophene carboxylic acid. 4,6-dihydrothieno-[3,4-b]-thiophene carboxylic acid is fluorinated by sequential treatment of n-butyl lithium (n-BuLi) followed by N-fluorobenzene sulfonamide (NFSI) to yield 3-fluoro-4,6-dihydrothieno-[3,4-b]-thiophene carboxylic acid. The 3-fluoro-4,6-dihydrothieno-[3,4-b]-thiophene carboxylic acid is then reacted with oxalyl chloride in dimethyl formamide (DMF) to yield 3-fluoro-4,6-dihydrothieno-[3,4-b]-thiophene carbonyl chloride. 3-fluoro-4,6-dihydrothieno-[3,4-b]-thiophene carbonyl chloride is treated with an alkanol in the presence of triethyl amine and dichloromethane (DCM) to yield 3-fluoro-4,6-dihydrothieno-[3,4-b]-thiophene alkyl ester. 3-fluoro-4,6-dihydrothieno-[3,4-b]-thiophene alkyl ester is then reacted with meta-chloroperbenzoic acid (mCPBA) in ethyl acetate (AcOEt) to yield an S-oxyl derivative. The S-oxyl derivative is cyclized by refluxing acetic anhydride ($Ac_2O$) to form 3-fluoro-thieno-[3,4-b]thiophene alkyl ester. The 3-fluoro-thieno-[3,4-b]thiophene alkyl ester is then brominated with N-bromosuccinimide (NBS) to yield F-MTT. Overall, the synthesis of F-MTT shown in FIG. 3 involves at least 12 reactions (including generating MOMCl) and 18 purification steps.

Overall, syntheses of MTT and F-MTT described herein provide fewer reactions and purification steps than typical MTT and F-MTT syntheses. F-MTT and MTT syntheses described herein provide F-MTT and MTT products with higher overall yields (due to the fewer number of reactions and purifications as compared to typical syntheses). F-MTT and MTT syntheses described herein provide F-MTT and MTT products at much lower overall cost, as compared to typical F-MTT and MTT syntheses, due to the fewer number of reactions and purifications which allows fewer purchases/syntheses of starting materials, reaction solvents, extraction media, recrystallization solvents, solid phase material for chromatography, energy input to a distillation apparatus, etc. The cost advantage and reduced overall amounts of material render syntheses of MTT and F-MTT (and derivatives thereof) amenable for industrial application/scale-up. Furthermore, reagents such as $SnCl_2$ (and byproducts thereof) and oxalyl chloride can be avoided using MTT and F-MTT syntheses described herein. Furthermore, 3-iodo-thieno-[3,4-b]-thiophene (1) is a versatile compound/intermediate that can be transformed into MTT, F-MTT, and derivatives thereof useful for small molecule and polymer photovoltaic applications.

While the foregoing is directed to embodiments of the present disclosure, other and further embodiments of the present disclosure may be devised without departing from the basic scope thereof.

We claim:
1. A method for synthesizing a compound comprising:
mixing a 3-(methylthio)-4-alkynylthiophene with iodine or iodine monochloride to form a 3-iodo-thieno-[3,4-b]thiophene;
fluorinating the 3-iodo-thieno-[3,4-b]thiophene to form a 3-fluoro-thieno-[3,4-b]thiophene; and
mixing the 3-fluoro-thieno-[3,4-b]thiophene with a halogenating agent to form a compound of the structure

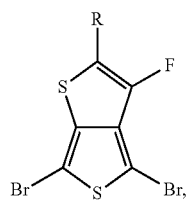

wherein R is selected from the group consisting of alkyl, ester, aryl, vinyl, ketone, amide, and sulfone.

2. The method of claim 1, further comprising forming the 3-(methylthio)-4-alkynylthiophene by reacting a 3-bromo-4-(methylthio)-thiophene with a terminal alkyne.

3. The method of claim 2, further comprising forming the 3-bromo-4-(methylthio)-thiophene by mixing 3,4-dibromo-thiophene with n-butyl lithium to form a first mixture and adding dimethyl disulfide to the first mixture to form a second mixture.

4. The method of claim 2, wherein the method further comprises mixing copper iodide and an amine with the 3-bromo-4-(methylthio)-thiophene and the terminal alkyne.

5. The method of claim 1, wherein the fluorinating includes reacting the 3-iodo-thieno-[3,4-b]thiophene with silver fluoride.

6. The method of claim 1, wherein the fluorinating includes mixing 3-iodo-thieno-[3,4-b]-thiophene with 3 molar equivalents of (t-ButylCN)$_2$CuOTf and 2 molar equivalents of silver fluoride in N,N-dimethylformamide solvent to form a mixture; and heating the mixture to between about 110° C. and about 170° C.

7. The method of claim 5, wherein reacting includes mixing cesium fluoride with the 3-iodo-thieno-[3,4-b]thiophene and the silver fluoride.

8. The method of claim 1, wherein the halogenating agent is N-bromosuccinimide or bromine.

9. A compound of the structure:

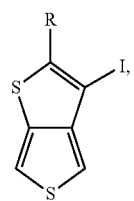

wherein R is selected from the group consisting of alkyl, ester, aryl, vinyl, ketone, amide, and sulfone.

10. The compound of claim 9, wherein R is substituted with an electron withdrawing group.

11. The compound of claim 10, wherein the electron withdrawing group is selected from the group consisting of —F, —Cl, —Br, —I, —CF$_3$, and nitro.

12. The compound of claim 9, wherein R is substituted with an electron donating group.

13. The compound of claim 12, wherein the electron donating group is alkyl or alkoxy.

14. A method for synthesizing a compound, the method comprising:
reacting a 3-bromo-4-(methylthio)-thiophene with a terminal alkyne to form a 3-(methylthio)-4-alkynylthiophene; and
cyclizing the 3-(methylthio)-4-alkynylthiophene to form a 3-iodo-thieno-[3,4-b]-thiophene; and
fluorinating and brominating the 3-iodo-thieno-[3,4-b]-thiophene to form a compound of the structure

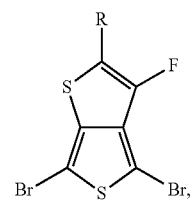

wherein R is selected from the group consisting of alkyl, ester, aryl, vinyl, ketone, amide, and sulfone.

15. A method for synthesizing a compound comprising:
forming a 3-(methylthio)-4-alkynylthiophene by mixing a 3-bromo-4-(methylthio)-thiophene, a terminal alkyne, and Pd(PPh$_3$)$_4$;
mixing the 3-(methylthio)-4-alkynylthiophene with iodine or iodine monochloride to form a 3-iodo-thieno-[3,4-b]thiophene;
fluorinating the 3-iodo-thieno-[3,4-b]thiophene to form a 3-fluoro-thieno-[3,4-b]thiophene; and
mixing the 3-fluoro-thieno-[3,4-b]thiophene with a halogenating agent to form a compound of the structure

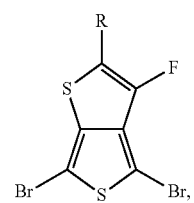

wherein R is selected from the group consisting of alkyl, ester, aryl, vinyl, ketone, amide, and sulfone,
wherein the 3-(methylthio)-4-alkynylthiophene is selected from the group consisting of:

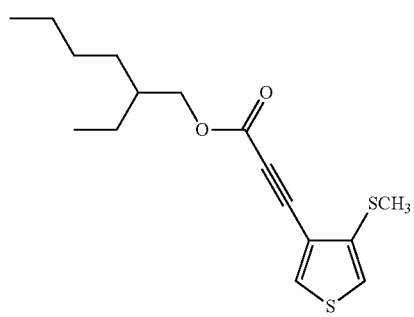

23
-continued
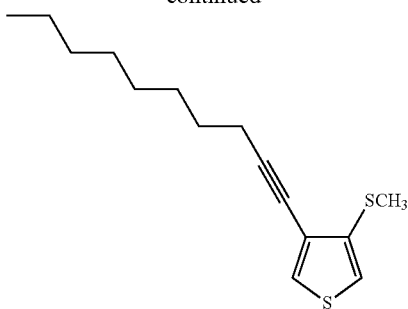
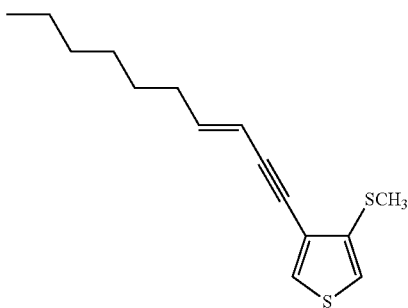
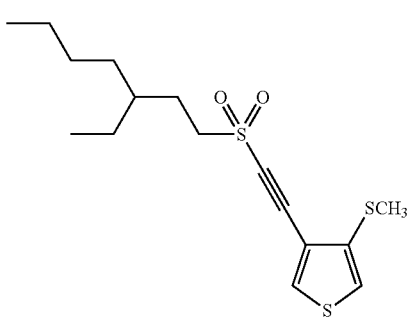
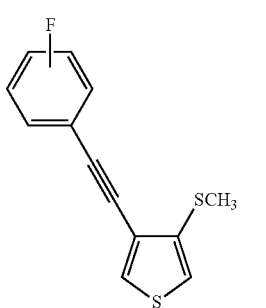
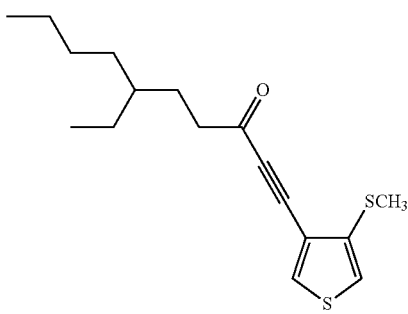
24
-continued
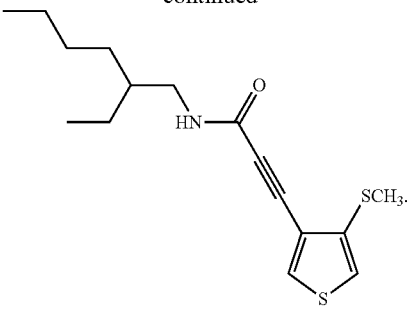
16. A method for synthesizing a compound comprising:
mixing a 3-(methylthio)-4-alkynylthiophene with iodine or iodine monochloride to form a 3-iodo-thieno-[3,4-b]thiophene selected from the group consisting of:
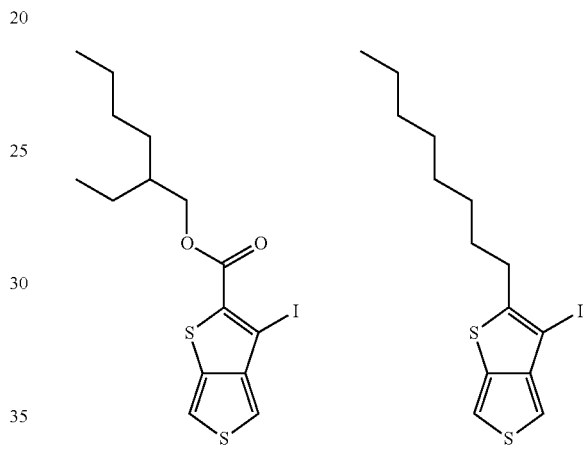
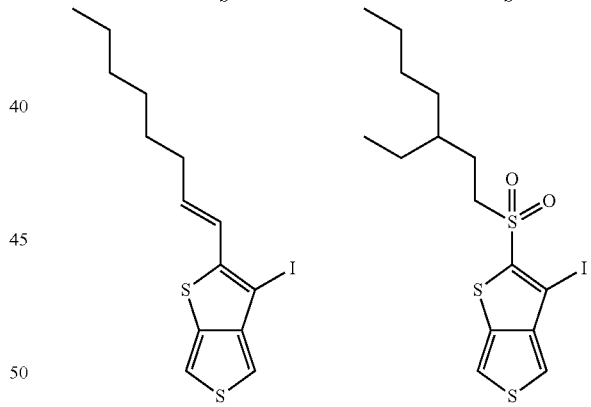
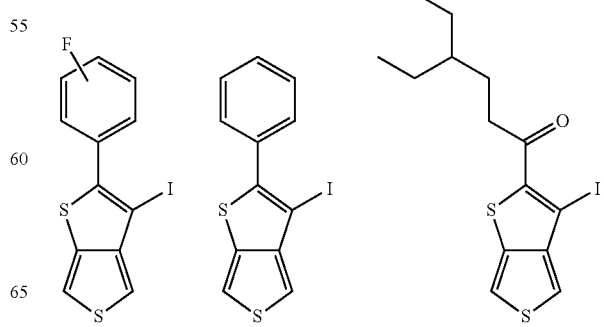

-continued

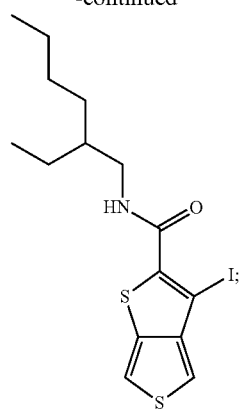

fluorinating the 3-iodo-thieno-[3,4-b]thiophene to form a 3-fluoro-thieno-[3,4-b]thiophene; and mixing the 3-fluoro-thieno-[3,4-b]thiophene with a halogenating agent to form a compound of the structure

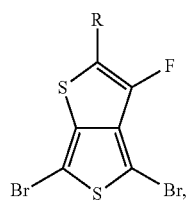

wherein R is selected from the group consisting of alkyl, ester, aryl, vinyl, ketone, amide, and sulfone.

17. A method for synthesizing a compound comprising:
mixing a 3-(methylthio)-4-alkynylthiophene with iodine or iodine monochloride to form a 3-iodo-thieno-[3,4-b]thiophene of the structure:

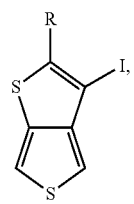

wherein R is selected from the group consisting of alkyl, ester, aryl, vinyl, ketone, amide, and sulfone;

fluorinating the 3-iodo-thieno-[3,4-b]thiophene to form a 3-fluoro-thieno-[3,4-b]thiophene, wherein the fluorinating includes mixing the 3-iodo-thieno-[3,4-b]thiophene with silver fluoride and (t-ButylCN)₂CuOTf;

mixing the 3-fluoro-thieno-[3,4-b]thiophene with a halogenating agent to form a compound of the structure

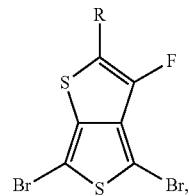

wherein R is selected from the group consisting of alkyl, ester, aryl, vinyl, ketone, amide, and sulfone.

18. The compound of claim 9 selected from the group consisting of:

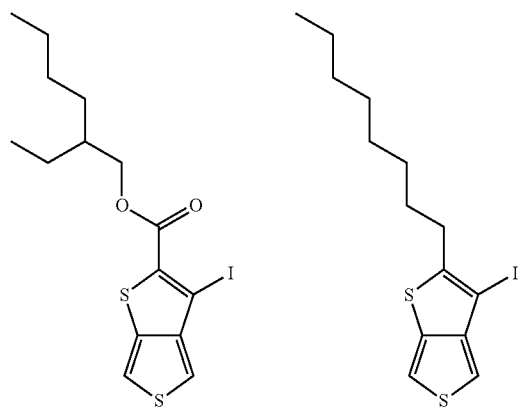

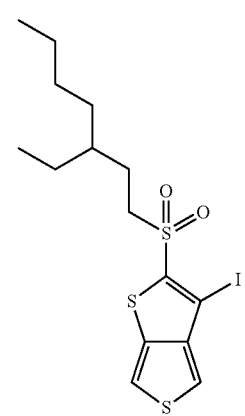

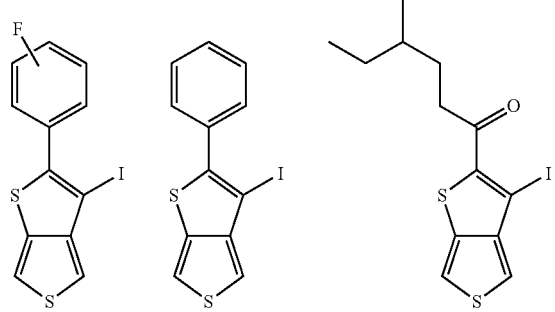

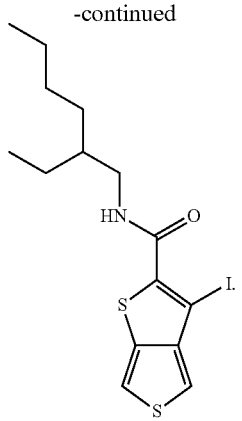
* * * * *